(12) United States Patent
Pflaum

(10) Patent No.: US 6,838,566 B2
(45) Date of Patent: *Jan. 4, 2005

(54) SALTS OF HMG-COA REDUCTASE INHIBITORS

(75) Inventor: Zlatko Pflaum, Domzale (SI)

(73) Assignee: LEK Pharmaceuticals d.d., Ljubljana (SI)

( * ) Notice: Subject to any disclaimer, the term of this patent is extended or adjusted under 35 U.S.C. 154(b) by 0 days.

This patent is subject to a terminal disclaimer.

(21) Appl. No.: 10/320,285

(22) Filed: Dec. 16, 2002

(65) Prior Publication Data

US 2003/0120086 A1 Jun. 26, 2003

Related U.S. Application Data

(63) Continuation of application No. 09/787,387, filed as application No. PCT/IB99/01554 on Sep. 17, 1999, now Pat. No. 6,583,295.

(30) Foreign Application Priority Data

Sep. 18, 1998 (SI) ............................................. P-9800240

(51) Int. Cl.[7] .................. C07C 69/13; C07C 69/30; C07C 211/07; C07C 211/14; C07C 309/30
(52) U.S. Cl. ...................... 548/537; 548/494; 549/292; 560/248; 560/256
(58) Field of Search ................. 548/537, 474; 549/292; 560/248, 256

(56) References Cited

U.S. PATENT DOCUMENTS

| | | | |
|---|---|---|---|
| 4,319,039 A | 3/1982 | Albers-Schonberg | ....... 560/256 |
| 4,342,767 A | 8/1982 | Albers-Schonberg | ....... 424/250 |
| 4,346,227 A | 8/1982 | Terahara et al. | ............ 560/119 |
| 5,223,415 A | 6/1993 | Conder et al. | .............. 435/125 |
| 5,356,896 A | 10/1994 | Kabadi et al. | |
| 5,403,860 A | 4/1995 | Kurabayashi et al. | ....... 514/460 |
| 5,763,646 A | 6/1998 | Kumar et al. | ................ 560/252 |
| 5,763,653 A | 6/1998 | Khanna et al. | ............. 560/252 |

FOREIGN PATENT DOCUMENTS

| | | | | |
|---|---|---|---|---|
| EP | 0 065 835 B1 | 11/1985 | ......... | C07D/309/30 |
| EP | 0 456 214 A1 | 11/1991 | ......... | C07D/309/30 |
| GB | 2 055 100 A | 2/1981 | ........... | C07C/69/00 |
| HU | 217629 B | 11/1992 | .......... | A61K/31/40 |
| HU | 221849 B1 | 11/1992 | .......... | A61K/31/40 |
| JP | 57-123140 A | 7/1982 | ......... | A61K/31/215 |
| JP | 57-123140 | 7/1982 | ......... | A61K/31/215 |

Primary Examiner—Brian Davis
(74) Attorney, Agent, or Firm—Cohen, Pontani, Lieberman & Pavane

(57) ABSTRACT

Lovastatin, pravastatin, simvastatin, mevastatin, atorvastatin, and derivatives and analogs thereof are known as HMG-CoA reductase inhibitors and are used as antihypercholesterolemic agents. The majority of them are produced by fermentation using microorganisms of different species identified as species belonging to Aspergillus, Monascus, Nocardia, Amycolatopsis, Mucor or Penicillium genus, some are obtained by treating the fermentation products using the methods of chemical synthesis or they are the products of total chemical synthesis. The present invention relates to the new amine salts of HMG-CoA reductase inhibitors, the preparation thereof, the preparation of pure HMG-CoA reductase inhibitors via amine salts thereof, use of the amine salts of HMG-CoA reductase inhibitors in the process for semisynthetic preparation of HMG-CoA reductase inhibitors, use of the amine salts of HMG-CoA reductase inhibitors in the process for biotechnological modification of HMG-CoA reductase inhibitors as well as the conversion of the amine salts of HMG-CoA reductase inhibitors into the pharmaceutically acceptable salts of the HMG-CoA reductase inhibitors and the conversion of the amine salts of HMG-CoA reductase inhibitors into the HMG-CoA reductase inhibitors in the lactone form.

48 Claims, No Drawings

SALTS OF HMG-COA REDUCTASE INHIBITORS

The present application is a continuation of U.S. patent application Ser. No. 09/787,387 filed on Apr. 25, 2001 now U.S. Pat. No. 6,583,295 filed Apr. 25, 2001, which is based on International Application No. PCT/IB99/01554, filed Sep. 17, 1999. These applications are incorporated herein by reference.

TECHNICAL FIELD AND BACKGROUND ART

Lovastatin, pravastatin, simvastatin, mevastatin, atorvastatin and derivatives and analogs thereof are examples of known as HMG-CoA reductase inhibitors which are used as antihypercholesterolemic agents. The majority of them are produced biotechnologically by fermentation using microorganisms of different species identified as species belonging to Aspergillus, Monascus, Nocardia, Amycolatopsis, Mucor or Penicillium genus, some are obtained by treating the fermentation products using the methods of chemical synthesis, thus leading to semi-synthetic substances, or they are the products of total chemical synthesis.

The present invention relates to a new industrial process for isolation and/or purification of HMG-CoA reductase inhibitors via salt thereof with specific amines. The invention enables a user to obtain the pure amine salts of HMG-CoA reductase inhibitors from the fermentation broth in case the substances are produced by biotechnological (microbiological) processes, or from the rection mixture in case the substances are produced by semisynthetic or total chemical synthesis. The step of forming salts with amine may be one of the steps in the process for isolation and/or purification of HMG-CoA reductase inhibitors or precursor substances thereof. The amines described in the present specification are very useful for the formation of salts in the composition of media in processes for biotechnological modification of HMG-CoA reductase inhibitors or precursors thereof. The salts thus formed may be used as the starting substances or intermediates for the preparation of semisynthetic drivatives and analogs thereof, or by employing simple techniques known from the literature, if required, to be converted into the pharmaceutically acceptable salts and lactones, respectively.

The processes for the isolation and purification of antihypercholesterolemic agents known from patent and technical literature include different combinations of extraction, chromatography, lactonization and crystallization methods. Some of them additionally include the isolation and purification via different salts. In U.S. Pat. Nos. 9,342,767 and 4,319,039, the ammonium salt of lovastatin (in the carboxylate form) is isolated directly from the organic phase which has been extracted from the fermentation medium. In the same patent the preparation of ethylenediamine, tetramethylammonium, potassium and N-methylglucamine salts as well as the salts of different amino acids such as L-lysine, L-arginine and L-ornithine is also described. The aforementioned salts are prepared from the already purified substance and the option for their use in the process of isolation or purification is not mentioned. GB 2055100A also describes the formation of the sodium and calcium salts of lovastatin, which comprises the extraction in methanol, two steps of preparative liquid reverse-phase chromatography, crystallization from methanol and recrystallization from ethanol, and the conversion into the salt using an aqueous solution of sodium or calcium hydroxide. However, without including various chromatography methods, the methods described do not yield a product of the purity comparable to the product obtained by using the present invention. U.S. Pat. No. 4,346,227 discloses a process for the preparation of the sodium salt of pravastatin, wherein chromatographic techniques are also used but the final product is obtained only after lyophilization which is not an economical process in a large scale production operations. EP 65,835 discloses the preparation of the L-ornithine and t-octylamine salts of tetrahydro-M-4 or tetrahydro-IsoM-4 (wherein M4 denotes a specific HMG-CoA reductase inhibitor, M-4 and IsoM-4 representing the isomers hydroxylated at 6- and 3-biphenyl ring position, respectively, and "tetrahydro" means that the condensed biphenyl ring system is fully hydrogenated) as final products, that is from the respectively purified sodium salts thereof, but not as intermediates via which the isolation would be carried out. Other salts of tetrahydro- M-4 or IsoM-4 with ammonia, an amino acid or an organic amine are also contemplated as final products, including octylamine, 2-ethylhexylamine, benzylamine, α-methyl benzylamine, phenethylamine, dibenzylamine, N-methylbenzylamine, N,N-dimethylbenzylamine, N,N-diethylbenzylamine, N-ethyl-N-methylbenzylamine, tribenzylamine, cyclopentylamine, cyclohexylamine cycloheptylamine, N-methylcyclopentylamine, N-ethylcyclohexylamine, N-ethylcycloheptylamine, dicyclohexylamine, N,N-dimethylcyclopentylamine, N,N-dimethylcyclopentylamine, N,N-diethylcycloheptylamine, pyrrolidine, N-methylpyrrolidine, piperidine, N-methylpiperidine and morpholine. GB 2073199A also discloses the preparation of different salts of HMG-CoA reductase inhibitors from the already isolated substance in the lactone form. U.S. Pat. Nos. 5,763,653 and 5,763,646 disclose the preparation of the cyclopropylamine and n-butylamine amides of lovastatin and their use in a process of chemical semisynthesis of simvastatin. U.S. Pat. No. 5,403,860 discloses, as final products, amine salts of octahydronaphthalene oxime derivatives of HMG-CoA inhibitors, the derivatives deriving from ML-236A, ML-236B, MB-530A and MB-530B. As final amine salts t-octylamine, dibenzylamine, dicyclohexylamine, morpholine, D-phenylglycine alkylester and D-glucosamine salts are mentioned.

Technical Problem

In industry there exists a constant need for rationalization of the production and shortening of the production processes as well as for the use of least expensive starting raw materials or intermediate substances. To date the isolation of the final products in the case of HMG-CoA reductase inhibitors has been a multi-stage process wherein each step adds its share to the losses resulting in the final yield rarely greater than 60%. In addition, a product in the lactone form or lactone converted into the sodium salt is used as the starting substance in the process of semisynthesis (e.g. in a process for preparing simvastatin) or biochemical conversion (e.g. in a process for preparing pravastatin). The preparation of lactone is one of the least economical steps in the production of HMG-CoA reductase inhibitors since losses in the course of the conversion from the acid into the lactone form and optionally further into the salts are greater than 20%. Therefore, there is a constant need for the starting substances and/or the intermediate substances which would be sufficiently pure, with small losses during their conversion, low costs, and the preparation per se should be technologically simple.

SUMMARY OF THE INVENTION

In our developmental and research work we have surprisingly found that HMG-CoA reductase inhibitors form the salts with certain amines which crystallize from mother liquor once they are formed. It has surprisingly been found that crystals of the amine salt of the desired HMG-CoA reductase inhibitor of high purity may be obtained from the liquors containing a large number of impurities and undesired HMG-CoA reductase inhibitor analogs. Contrary to the statements from U.S. Pat. No. 5,403,860 that lower yields are obtained when using the salts of HMG-CoA reductase inhibitor as starting or intermediate substances in a process for preparing the substances (Ia) mentioned below, we have surprisingly found that, when using the amine salts of HMG-CoA reductase inhibitors according to the present invention, the yields and the purity of the prepared HMG-CoA reductase inhibitors are equal to or greater than when using the HMG-CoA reductase inhibitors in the lactone form.

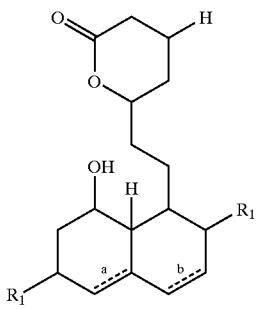

Furthermore, we surprisingly discovered that in processes for the biotechnological modification of HMG-CoA reductase inhibitors the formation of amine salts of HMG-CoA reductase inhibitors in the medium which derives from the fermentation liquor provides, in comparison with the mere metal salts as described in publicly accessible literature, an efficient means for the isolation and/or purification of HMG-CoA reductase inhibitors by means of simple crystallization. The amines which are described in the present specification and which readily form salts with HMG-CoA reductase inhibitors are thus particularly suitable as auxiliary materials or processing aids for the isolation and/or purification of HMG-CoA reductase inhibitors. Furthermore, they can be excellently used as starting materials or intermediates of semisynthetic preparation or biotechnological modification of HMG-CoA reductase inhibitors and, furthermore, for the conversion into pharmaceutically acceptable salts or into the lactone form of the respective HMG-CoA reductase inhibitors. Accordingly, the novel amine salts of HMG-CoA reductase inhibitors of the present invention are also highly valuable as such.

The present invention provides:
a) the novel salts of HMG-CoA reductase inhibitors with organic amines, wherein those specific salts are excluded which are disclosed in the prior art, but in different contexts as mentioned above,
b) a process for the preparation of salts of HMG-CoA reductase inhibitors with amines,
c) a use of salts of HMG-CoA reductase inhibitors with amines as processing aids or starting substances or intermediate substances in various processes,
d) a process for the preparation of the pure HMG-CoA reductase inhibitors from/via amine salts thereof,
e) a process for the semisynthetic preparation of HMG-CoA reductase inhibitors, wherein the amine salts of HMG-CoA reductase inhibitors are used as the starting substances,
f) a process for the biotechnological modification of HMG-CoA reductase inhibitors, wherein one of the components of the medium is the amine salt of HMG-CoA reductase inhibitors,
g) a process for the conversion of the amine salts of HMG-CoA reductase inhibitors into the pharmaceutically acceptable salts of HMG-CoA reductase inhibitors, and
h) a process for the conversion of the amine salts of HMG-CoA reductase inhibitors into HMG-CoA reductase inhibitors in the lactone form.

The amine which is used according to the present invention for the formation of the salts with a HMG-CoA reductase inhibitor is selected from the group consisting of organic amines of the following formulae I and II:

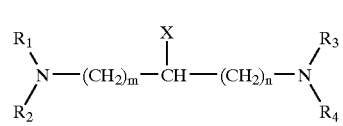

wherein:
a1) $R_1$, $R_2$, $R_3$, and $R_4$ independently denote
a hydrogen atom
a straight or branched alkyl group having 1 to 8 carbon atoms, or
a cycloalkyl group having 3 to 8 carbon atoms, or
an arylalkyl group wherein the alkyl group is methyl or ethyl and the aryl group is phenyl, which is optionally substituted by an N-alkyl or N,N-dialkyl group wherein the alkyl group is alkyl having 1 to 4 carbon atoms, or
an arylalkyl group which is optionally substituted by one or more substituents,
a hydroxyalkyl group having 2 to 4 carbon atoms, or
an aminoalkyl group having 2 to 4 carbon atoms, which are optionally substituted by an N-alkyl or N,N-dialkyl group wherein the alkyl group is alkyl having 1 to 4 carbon atoms;
X denotes a hydrogen atom, a hydroxyl group, a halogen or a methyl group; m and n independently denote an integer from 0 to 5; or
a2) $NR_1R_2$ or $NR_3R_4$ denote a heterocyclic ring having 3 to 7 methylene groups, one of these groups being optionally substituted by an oxygen or a sulfur atom or an amine group; X, m and n are as defined above;

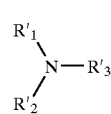

wherein:
b1) $R'_1$, $R'_2$, and $R'_3$ are the same or different and denote hydrogen, alkyl, alkenyl, amino- or hydroxy-or alkoxy-substituted alkyl or alkenyl, or substituted amino-alkyl or alkenyl, provided that $R'_1$, $R'_2$, and $R'_3$ are not hydrogen at the same time; or
b2) $R'_1$, and $R'_2$, and optionally $R'_3$, together with the nitrogen atom form an optionally substituted heterocyclic ring system including the nitrogen atom as a ring member, and optionally including an additional hetero atom, and if, $R'_3$ is not part of the ring system it is independently selected from hydrogen, alkyl, alkenyl, amino- or hydroxy- or alkoxy-substituted alkyl, or substituted amino-alkyl; or b3) R'₁, is a group of general formula III,

   III wherein m is zero or an integer from 1 to 5, R' is optionally substituted aliphatic hydrocarbon cyclic system having 3 to 8 carbon atoms in the ring, R'₄ is hydrogen, or alkyl, amino- or hydroxy- or alkoxy-substituted alkyl, or substituted amino-alkyl, or a group of the same general formula as R'₁ as defined herein above; R'₂ and R'₃ are the same as R'₁ or hydrogen, alkyl, alkenyl, amino- or hydroxy- or alkoxy-substituted alkyl, or substituted amino-alkyl or alkenyl; or b4) R'₁ is an optionally substituted aryl group of general formula IV;

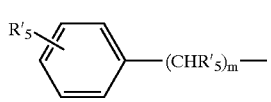   IV wherein R'₅ is hydrogen and one or more substituents, and m is zero or in integer from 1 to 5; and R'₂ and R'₃ may be independently hydrogen, alkyl, amino- or hydroxy- or alkoxy-substituted alkyl, or substituted amino-alkyl, or groups of the same general formula R'₁

Substitutions which are not explicitly specified are usual "inert" substituents, such as halogens, a hydroxyl group, alkyl having 1 to 4 carbon atoms, alkoxyl having 1 to 4 carbon atoms, acyloxyl having 1 to 4 carbon atoms and esterified carboxyl having 1 to 4 carbon atoms.

Advantageous examples of amines which form the salt with HMG-CoA reductase inhibitors are: (±)-1,2-dimethylpropylamine, 3-(2-aminoethylamino)-propylamine, n-butylamine, secondary butylamine, tertiary butylamine (TBA), dibutylamine, tertiary amylamine, cyclopentylamine, cyclohexylamine, cycloheptylamine, dicyclohexylamine (DCHA), N-methylcyclohexylamine, N,N'-diisopropylethylenediamine (DIPEDA), N,N'-diethylenediamine, N-methyl-1,3-propanediamine, N-methylethylenediamine, N,N,N',N'-tetramethyl-1,2-diaminoethane, N,N,N',N'-tetramethyl-1,4-diaminobutane, N,N,N',N'-tetramethyl-1,6-diaminohexane, 1,2-dipiperidinethane, dipiperidinemethane, 2-amino-3,3-dimethylbutane, N,N-dimethylcyclohexylamine, neopentylamine, adamantylamine, N,N-diethylcyclohexylamine, N-isopropylcyclohexylamine, N-methylcyclohexylamine, cyclobutylamine and norborylamine. Preferably in terms of crystallization efficiency, combined with low toxicity and low costs, the amine is selected from the group consisting of n-butylamine, secondary butylamine, TBA, dibutylamine, tertiary amylamine, cyclohexylamine, DCHA, N-methylcyclohexylamine and DIPEDA. The amine may particularly be selected from the group consisting of TBA, DIPEDA, DCHA and N-methylcyclohexylamine.

The amines specified above are advantageous over the direct isolation via the salts with ammonia in terms of purification efficiency. Furthermore, amines having a larger organic group, and especially those having bulky groups, generally show a more readily crystallization and to a lower extent form salts with unwanted side products when compared with amines having small organic groups. Accordingly, amines having at least one hydrocarbon residue with secondary or tertiary carbon atoms, or with cyclic hydrocarbon structure (either aromatic or aliphatic), and organic diamines are particularly suitable for the present invention.

Any type of HMG-CoA reductase inhibitors can be used according to the present invention. Those HMG-CoA reductase inhibitors selected from the group consisting of mevastatin, pravastatin, lovastatin, simvastatin, fluvastatin and atorvastatin have shown good results and are particularly preferred.

For isolating and purifying the desired HMG-CoA reductase inhibitor, the amine salt is most effectively formed directly from the crude medium of the respective HMG-CoA reductase inhibitor, which crude medium is usually derived from a fermentation broth as the result of a biotechnological process or from a reaction mixture as the result of a semisynthesis or the total synthesis and usually contains the desired HMG-CoA reductase inhibitor together with unwanted side products and impurities. The crude medium may preferably contain the HMG-CoA reductase inhibitor in its acid from, and the formation of the amine salt may be effected by simply adding the amine to the crude medium. The crude medium may be an organic phase or a mixture of an organic or an aqueous phase where the impure HMG-CoA reductase inhibitor is present in an organic solvent, such as ethyl acetate, ether or acetonitrile. Ethyl acetate is preferred as the organic solvent. After the biotechnological treatment, the crude medium in the organic phase is preferably obtained from the fermentation broth by a process including the step of extracting the HMG-CoA reductase inhibitor into the aforementioned organic solvent.

The process for the preparation of the amine salts of HMG-CoA reductase inhibitors may include the following steps:

a) contacting the medium containing the HMG-CoA reductase inhibitor, which is preferably in the acid form in an organic solvent, with at least one of the amines specified above, b) optionally forming crystallization nuclei by known techniques, c) filtering the crystals crystallized out, d) washing the crystals with an organic solvent, and e) drying the crystals.

The term "contacting" includes the known techniques for the preparation of the salts from substances with acid properties and substances with alkaline properties. The crystallization is preferably carried out at a temperature between 0 and 30° C., more preferably between 4 and 22° C.

The term "organic solvent" means organic solvents which are used in industry such as ethyl acetate, butyl acetate, ether and acetonitrile, including their aqueous mixtures.

Since the amines specified above effectively form salts with the HMG-CoA reductase inhibitors, they are also particularly suitable as auxiliary materials or processing aids in a process for preparing the HMG-CoA reductase inhibitor in a purified form. Previously isolated HMG-CoA reductase inhibitors can be thus obtained in a higher purity. The purified form is usually prepared by crystallization. Accordingly, the present invention provides a process for the isolation and/or purification of a HMG-CoA reductase inhibitor.

In further aspects of the present invention, the salt as specified above is suitably used as the starting substance or the intermediate substance in a process for preparing the HMG-CoA reductase inhibitor which is in a modified form, in a pharmaceutically active salt form or in the lactone form. Specifically, the modified form is obtained by chemical modification or biotechnological modification, which modifications are known to those skilled in the art. The pharmaceutically active salt is preferably a metal salt, such as the sodium salt or the calcium salt.

In this connection, the term "a process for the semi-synthetic preparation of HMG-CoA reductase inhibitors" means the preparation of HMG-CoA reductase inhibitors using any of the known chemical modifications of the HMG-CoA reductase inhibitors. An example of such process is the semisynthesis of simvastatin from lovastatin as the starting substance. Most preferably, the TBA salt of lovastatin is used as the starting substance.

Furthermore, the term "a process for the biotechnological modification of HMG-CoA reductase inhibitors" means the preparation of HMG-CoA reductase inhibitors using microorganisms or enzymatic systems thereof for modifying HMG-CoA reductase inhibitors. An example of such process is the biotechnological conversion of mevastatin into pravastatin. The amine salt is preferably the TBA salt.

Furthermore, the term "a process for the conversion of the amine salts of HMG-CoA reductase inhibitors into the pharmaceutically acceptable salts of HMG-CoA reductase inhibitors" includes processes for the preparation of HMG-CoA reductase inhibitors by one of the known methods wherein the amine salts of HMG-CoA reductase inhibitors are used as the starting substance. Specific examples or converted salts are the sodium salts of pravastatin and fluvastatin and the calcium salt of atorvastatin.

Furthermore, the term "conversion of the amine salts of HMG-CoA reductase inhibitors into HMG-CoA reductase inhibitors in the lactone form" includes processes for the preparation of HMG-CoA reductase inhibitors in the lactone form by one of the known methods wherein the amine salts of HMG-CoA reductase inhibitors are used as the starting substance. Examples of HMG-CoA reductase inhibitors converted into the lactone form are lovastatin, mevastatin or simvastatin.

The present invention is illustrated but in no way limited by the following examples.

EXAMPLES

Example 1
Preparation of Free Acid of Mevastatin and Conversion thereof into Salt thereof with Tertiary Butylamine (TBA)

Mevastatin (200 g) was suspended in 30% volume/volume (v/v) aqueous acetonitrile solution (2500 ml), 3 equivalents of triethylamine were added and the mixture was heated to 80° C. and stirred for 30 minutes. After the completed reaction, acetonitrile was evaporated, the remaining solution was acidified to pH 4 with phosphoric acid and extracted into ethyl acetate (2×1000 ml). The pooled extracts were dried by the addition of 30 g of sodium sulphate, the desiccant was filtered off and the solution was concentrated (950 ml). TBA (1.5 equivalents) was added to the solution and crystallization was carried out for 30 minutes at 8° C. The crystals formed were filtered and washed with ethyl acetate (2×100 ml) and subsequently dried at 40° C. for 15 hours. The crystals obtained (the TBA salts of mevastatin 215 g) were white in color with a HPLC purity of 96.8%. The yield of the hydrolysis and crystallization was 91%.

Example 2
Preparation of the Sodium Salt of Mevastatin from the TBA Salt of Mevastatin The TBA salt of mevastatin (1 g), obtained by the process disclosed in example 1, was dissolved in 3 ml of ethanol (96% v/v) and sodium hydroxide (40 g/L of ethanol) was added. The resulting mixture was precipitated in the ethyl acetate (60 ml). After the crystallization (30 min) at 8° C. the crystals were filtered off, washed with ethyl acetate and dried. The product: crystals of the sodium salt of mevastatin (0.65 g) pale brown in color with a HPLC purity of 98%.

Example 3
Isolation of the TBA Salts of Lovastatin from the Fermentation Broth

A fermentation broth (160 L) obtained by the fermentation with a microorganism Aspergillus terreus ATCC 20544 and having a lovastatin content of 1 g/L was transferred from the fermenter into the tank (400 L) and pH was adjusted to 10 with the addition of 1 M aqueous sodium hydroxide 10 minutes of vigorous stirring the pH of the broth was decreased to 9 by adding 1 M sulphuric acid solution and the biomass was filtered off. The filtrate obtained was acidified to a pH value of 6.5 with 1 M sulphuric acid solution and 160 L of ethyl acetate was added. The slurry was subsequently stirred for 20 minutes. The aqueous and ethyl acetate phases were separated by extraction centrifuge and the ethyl acetate extract was concentrated in a rotavapor to the volume of 14 L. The concentration of lovastatin in the form of free acid in concentrated ethyl acetate extract was 10.1 g/L. To the obtained lovastatin solution (HPLC purity 72.7%) in the form of free acid in ethyl acetate (800 ml) 1.05 equivalents of TBA were added. After crystals were crystallized out, they were filtered off, washed with ethyl acetate (2×50 ml) and dried in a vacuum oven at 35° C. for 24 hours. The yield: 8.06 g of crystals of the TBA salt of lovastatin with a HPLC purity of 99.2%.

Example 4
Preparation of the Salt of Lovastatin with Tertiary Amylamine

Lovastatin (5 g) was treated according to the process for hydrolysis disclosed in example 1 and sodium salt thereof (4.8 g) was prepared and dissolved in 100 ml of water. pH was adjusted to 4 with phosphoric acid (10% aqueous solution) and the formed free acid of lovastatin was extracted from the water phase into ethyl acetate (2×100 ml). The pooled ethyl acetate extracts were dried with sodium sulphate, the solution was filtered off and concentrated to ca. 100 ml. To the solution, prepared in the above manner (ca. 100 ml), 1.05 equivalents of tertiary amylamine were added. After crystals were crystallized out, they were filtered off, washed with ethyl acetate (2×10 ml) and dried in a vacuum oven (35° C., 24 hours). The yield: 4.8 g of crystals of the tertiary amylamine salt with a HPLC purity of 98.6%.

Example 5
Preparation of Pravastatin in the Free Acid Form and Conversion into the (±)-1,2-Dimethylpropylamine Salt thereof Pravastatin (11 g, HPLC purity 97.2%) in the form of Na salt was dissolved in water (100 ml) and pH was adjusted to 4 with phosphoric acid (10% aqueous solution). The resulting free acid was extracted from the water phase into ethyl acetate (2×100 ml). The pooled ethyl acetate extracts were dried with sodium sulphate, the solution was filtered off and concentrated to a volume of ca. 100 ml.

To the concentrate (9 ml) thus obtained, 1.5 equivalents of (±)-1,2-dimethyl-propylamine were added. After crystals were crystallized out, they were filtered off, washed with ethyl acetate (2×10 ml) and dried in a vacuum oven at 350° C. The yield: crystals yellow in color with a HPLC purity of 98.28%.

Examples 6–13
The Conversion of the Free Acid Form of Pravastatin into the Amine Salt Form as Described in Example 5 was Repeated with other Amines.

The amines used and results are shown in the Table below:

| Ex. | AMINE | EFFECT | HPLC purity |
|---|---|---|---|
| 6 | 3-(2 aminoethylamino)-propylamine | An oil is formed* | — |
| 7 | N,N$^1$-diisopropyl-ethylenediamine | Pale yellow crystals | 99.3% |
| 8 | N,N$^1$-diisopropyl-ethylenediamine | Yellow crystals | 99.3% |
| 9 | N-methyl-1,3-propanediamine | An oil is formed* | — |
| 10 | N-methylethylenediamine | An oil is formed | — |
| 11 | Secondary-butylamine | White crystals | 98.9% |
| 12 | Tertiary-butylamine (TBA) | Yellowish crystals | 97.4% |
| 13 | Tertiary - amylamine | Off-white crystals | 97.9% |

*from an oil formed, crystals are crystallized out overnight at 4° C.

Example 14
Preparation of the Salt of Pravastatin with Secondary Butylamine from the Crude Sodium Salt of Pravastatin According to the process described in example 5, pravastatin in the free acid form was prepared from the sodium salt of pravastatin (HPLC purity 83.6%). Further the salt or pravastatin with secondary butylamine was prepared by the process described in example 5. White crystals with a HPLC purity or 97.3% were obtained.

Example 15
Preparation of the Sodium Salt of Pravastatin from the TBA Salt of Pravastatin (1)

8.9 g of the TBA salt of pravastatin as obtained in example 12 were dissolved in 22 ml of ethanol (96%) and subsequently precipitated in 450 ml of ethyl acetate. Crystallization was carried out at 8° C. for 60 minutes, the crystals formed were filtered off, washed with two 50 ml portions of ethyl acetate and dried at 40° C. for 5 hours. 1 g of the recrystallized TBA salt of pravastatin, obtained in the above-described manner, was dissolved in 5 ml of ethanolic solution of 0.43N NaOH and precipitated in 60 ml of ethanol. After 30 minutes at 8° C., crystals formed were filtered off and dried. The formed crystals of the sodium salt of pravastatin (0.75 g) were dark yellow in color.

Example 16
Preparation of the Sodium Salt of Pravastatin from the TBA Salt of Pravastatin (2)

The process described in example 15 was repeated wherein 1 g of the recrystallized TBA salt of pravastatin was dissolved in 3 ml of water, instead of ethanolic solution of 0.43N NaOH, and subsequently an aqueous sodium carbonate solution (equivalent) was added. The obtained solution was diluted with 5 ml of ethanol and the resulting sodium salt was precipitated with ethyl acetate. After 30 minutes at 8° C., crystals formed were filtered off and dried. The formed crystals of the sodium salt of pravastatin (0.65 g) were yellow in color.

Example 17
Preparation of Pravastatin from the TBA Salt of Mevastatin
Preparation of Inoculum for Production The colonies of microorganism *Amycolatopsis orientalis* ATCC 19795 were transferred to a sterile potter and homogenized. The resulting colonies were transferred to agar slopes and incubated in the thermostat at 26° to 30° C. for 7 to 14 days. During that time surfaces of agar slopes were overgrown by cultures of homogeneous, folded, smooth, white to pale greyish-blue mycelium. Further, 10 ml of sterile water was poured onto the agar slopes, the culture was scraped off with the pipette and the contents transferred into the potter. A portion (0.5 to 1 ml) of the resulting culture was then inoculated into the vegetative medium.

| Agar medium for the preparation of agar slopes and petri plates. | |
|---|---|
| Raw material | Amount |
| Dextrin | 10 g |
| Consumer's glucose | 5 g |
| Casaminic acid | 3 g |
| Yeast extract | 4 g |
| Agar | 15 g |
| Sterile water | up to 1000 ml |

No pH adjustment needed.

Vegetative Phase of Fermentation

The inoculum grown on the slope at 26° to 30° C. for 10 days and prepared according to the above-described method was inoculated in a 500-ml Erlenmeyer flask containing 50 ml of the vegetative medium. After 24 hours of shaking at 220 rpm at 28° C., the culture was transferred onto the fermentation medium.

| Vegetative medium: | |
|---|---|
| Raw material | Amount |
| Corn starch for fermentation | 20 g |
| Soybean flour for fermentation | 14 g |
| Glucose | 10 g |
| Yeast extract | 5 g |
| NaH$_2$PO$_4$ × 2H$_2$O | 3.3 g |

Tap water to 1000 ml

Conversion of the TBA Salts of Mevastatin into Pravastatin

The contents of fifteen Erlenmeyer flasks with the culture, prepared according to the above-described method, were used to inoculate the fermenter (50 L) with 30 L of fermentation medium. After 20-hour fermentation, the solution of the TBA salt of mevastatin and glucose (1200 g of glucose and 70 g of TBA salt of mevastatin (assay of mevastatin: 80%) dissolved in 5 L of water) was continually added to the medium at the flow rate 2 ml/min. During the fermentation 70% oxygen saturation of the medium was maintained by stirring with the frequency between 300 and 600 rpm. Analyses of the concentration of pravastatin in the fermentation broth showed the total final concentration of pravastatin in the fermentation broth to be 690 g/kg of broth after 76 hours of fermentation at temperature between 24° and 30° C., indicating a 40% conversion of mevastatin into pravastatin.

| Fermentation medium: | |
|---|---|
| Raw material | Amount |
| Corn starch for fermentation | 20 g |
| Soybean flour for fermentation | 5 g |
| Glucose | 10 g |
| Yeast extract | 5 g |
| Antifoam agent | 10 g |

All raw materials were dissolved in tap water, the pH was then adjusted to 7.4.

Example 18
Preparation of TBA Salt of Simvastatin

Simvastatin (1.95 g) was suspended in 50 ml of 30% (v/v) acetonitrile, triethylamine (1 ml) was added and the solution was heated for 20 minutes at 70° C. After completion of reaction acetonitrile was evaporated from the solution, the remaining solution was acidified to pH 4 with phosphoric acid. Simvastatin in the acid form was extracted into ethyl acetate (2×50 ml) and the pooled extracts were dried with 2 g of sodium sulphate. The desiccant was filtered off and the ethyl acetate solution was concentrated to 20 ml. To the solution 1.05 equivalents of TBA were added and crystallization was carried out for 1 hour at 8° C. The product was filtered off and dried at 40° C. for 1 hour. The yield: 2 g of the TBA salt of simvastatin.

Example 19
Conversion of the TBA Salt of Simvastatin into Simvastatin Lactone The TBA salt of simvastatin (1.6 g), obtained by the process disclosed in example 18, was dissolved in water (36 ml), the solution was then acidified to pH 3.7 with an aqueous phosphoric acid solution and simvastatin in the acid form was extracted into ethyl acetate (2×50 ml). The pooled extracts were dried with sodium sulphate (2 g) and the desiccant was then filtered off. The ethyl acetate solution was concentrated to 20 ml.

To the solution trifluoroacetic acid (0.5 ml) was added and the reaction mixture was heated for 25 minutes at 50° C. After completion of the reaction, the ethyl acetate solution was extracted with 5% (w/w) aqueous solution of ammonium hydrogen carbonate. The organic phase was dried with sodium sulphate (2 g), the desiccant was filtered off and the ethyl acetate solution was concentrated to 4 ml. Crystallization was carried out for 1 hour at 8° C. The product was then filtered off and dried at 40° C. for 1 hour. The yield: 0.9 g of simvastatin in the acid form.

Example 20
Preparation of Free Acid of Simvastatin

Simvastatin (20 g) was dissolved in the mixture of water (80 ml) and 8M KOH (18 ml). The solution was stirred in nitrogen atmosphere for two hours at room temperature.

After that 120 ml of ethyl acetate was added and pH was adjusted to 2–3 with 5% aqueous solution of HCl. Ethyl acetate phase was washed with mixture of water (100 ml), 5% aqueous solution of HCl and 5% aqueous solution of NaCl (50 ml). The obtained ethyl acetate phase was then dried for three hours with addition of 20 g MgSO4 anhydrite and filtrated.

Preparation of Amine Salt

After that 18 ml of N-methylcyclohexylamine was added into the ethyl acetate phase. After two days at temperature between 0 and 5 degrees C. crystals of simvastatin N-methylcyclohexylamine salt were formed. Obtained crystals were filtered off and washed with 20 ml of ethyl acetate, 40 ml ethyl acetate/n-heptane (1:1) and 40 ml of pentane. The yield: 20.5 g of N-methylcyclohexylamine salt of simvastatin. The yield calculated to the starting simvastatin was 79%. The same results were obtained also with cyclohexylamine (by the use of the same method).

Example 21
Preparation of Pravastatin in Purified Form

Pravastatin (30 g, HPLC purity 90.2%) in the form of Na salt was dissolved in water (100 ml) and pH was adjusted to 3 with HCl (10% aqueous solution). The resulting free acid was extracted from the water phase into ethyl acetate (3×200 ml). The pooled ethyl acetate extracts were dried with sodium sulphate, the solution was filtered off and 7.604 g of N-methylcyclohexylamine was added (drop by drop at intensive stirring). After crystals were crystallized out, they were filtered off and recrystallized from the mixture of ethyl acetate/methanol. The yield: 21 g of crystals of pravastatin N-methylcyclohexylamine salt with a HPLC purity of 99.28%.

Example 22
Preparation of Free Acid of Atorvastatin

Calcium salt of atorvastatin (3 g) was suspended in 100 ml water. The pH was adjusted with the phosphoric acid to 4 and after that free acid of atorvastatin was extracted with ethyl acetate (3×100 ml ). Combined ethyl acetate extract was dried and 2.7 g of oil containing atorvastatin in the free acid form was obtained.

Preparation of Amine Salt 1 g of atorvastatin in the free acid form was dissolved in acetonitrile (100 ml) and 1.1 molar equivalents of TBA was added. The obtained mixture was concentrated to 30 ml and after four hours at 8° C. the TBA salt of atorvastatin crystallized. White precipitate was filtered off and dried in a rotary evaporator. Yield: 1 g of TBA salt of atorvastatin.

Example 23
Preparation of Amine Salt 1 g of atorvastatin in the free acid form was dissolved in methanol (20 ml) and 1.1 molar equivalents of dicyclohexylamine (DCHA) in 50 ml of n-hexane was added. After four hours at 8° C. the DCHA salt of atorvastatin crystallized. White precipitate was filtered off and dried in a rotary evaporator. Yield: 1.1 g of DCHA salt of atorvastatin.

What is claimed is:

1. A salt of a HMG-CoA reductase inhibitor with an amine, characterized in that said salt is an intermediate or a starting substance in a process for preparing the HMG-CoA reductase inhibitors, wherein the HMG-CoA reductase inhibitor is selected from the group consisting of mevastatin, pravastatin, lovastatin, simvastatin, fluvastatin and atorvastatin; and wherein the amine is selected from the group consisting of (±)-1,2-dimethylpropylamine, 3-(2-aminoethylamino)-propylamine, n-butylamine, secondary butylamine, tertiary butylamine, dibutylamine, tertiary amylamine, cyclopentylamine, cyclohexylamine, cycloheptylamine, dicyclohexylamine, N-methylcyclohexylamine, N,N'-diisopropylethylenediamine, N,N'-diethylenediamine, N-methyl-1,3-propanediamine, N-methylethylenediamine, N,N,N',N'-tetramethyl-1,2-diaminoethane, N,N,N',N'-tetramethyl-1,4-diaminobutane, N,N,N',N'-tetramethyl-1,6-diaminohexane, 1,2-dipiperidinethane, dipiperidinemethane, 2-amino-3,3-dimethylbutane, N,N-dimethylcyclohexylamine, neopentylamine, adamantylamine, N,N-diethylcyclohexylamine, N-isopropylcyclohexylamine, N-methylcyclohexylamine, cyclobutylamine and norborylamine.

2. The salt of a HMG-CoA reductase inhibitor with an amine according to claim 1, wherein the salt has a HPLC purity above 96%.

3. The salt of a HMG-CoA reductase inhibitor with an amine according to claim 1, wherein the salt has a HPLC purity above 97%.

4. The salt of a HMG-CoA reductase inhibitor with an amine according to claim 1, wherein the salt has a HPLC purity above 98%.

5. The salt of a HMG-CoA reductase inhibitor with an amine according to claim 1, wherein the salt has a HPLC purity above 99%.

6. A process for preparation of a salt of an HMG-CoA reductase inhibitor with an amine, characterized in that the amine is added to a crude medium of the HMG-CoA reductase inhibitor, wherein the HMG-CoA reductase inhibitor is selected from the group consisting of mevastatin, pravastatin, lovastatin, simvastatin, fluvastatin and atorvastatin; and wherein the amine is selected from the group consisting of (±)-1,2-dimethylpropylamine, 3-(2-aminoethylamino)-propylamine, n-butylamine, secondary butylamine, tertiary butylamine, dibutylamine, tertiary amylamine, cyclopentylamine, cyclohexylamine, cycloheptylamine, dicyclohexylamine. N-methylcyclohexylamine. N,N'-diisopropylethylenediamine, N,N'-diethylenediamine, N-methyl-1,3-propanediamine, N-methylethylenediamine, N,N,N',N'-tetramethyl-1,2-diaminoethane, N,N,N',N'-tetramethyl-1,4-diaminobutane, N,N,N',N'-tetramethyl-1,6-diaminohexane, 1,2-dipiperidinethane, dipiperidinemethane, 2-amino-3,3-dimethylbutane, N,N-dimethylcyclohexylamine, neopentylamine, adamantylamine, N,N-diethylcyclohexylamine, N-isopropylcyclohexylamine, N-methylcyclohexylamine, cyclobutylamine and norborylamine.

7. The process according to claim 6, wherein said crude medium is derived from a fermentation broth containing the crude HMG-CoA reductase inhibitor.

8. The process according to claim 6, wherein said crude medium has been obtained from the fermentation broth by a process including a step of extracting the crude HMG-CoA reductase inhibitor into an organic solvent.

9. The process according to claim 6, wherein said crude medium is derived from a reaction mixture containing the crude HMG-CoA reductase inhibitor.

10. The process according to claim 9, wherein said reaction mixture has been obtained by semi or total synthesis of the HMG-CoA reductase inhibitor.

11. The process according claim 6, wherein said crude medium is present in an organic solvent which is selected from the group consisting of ethylacetate, ether and acetonitrile.

12. The process according to claim 6, wherein the HMG-CoA reductase inhibitor in said crude medium is in the acid form.

13. The process according to claim 6, comprising the following steps:
a) contacting the medium containing the HMG-CoA reductase inhibitor with the amine;
b) optionally: conventionally forming crystallization nuclei;
c) filtering the crystals crystallized out;
d) washing the crystals with an organic solvent; and
e) drying the crystals.

14. The process according to claim 13, wherein the crystallization is carried out at temperature between 0 and 30° C.

15. The process according to claim 13, wherein the crystallization is carried out at temperature between 4 and 22° C.

16. A process for preparing a HMG-CoA reductase inhibitor (i) in a purified form;
(ii) in a modified form;
(iii) in a pharmaceutically active salt form; or
(iv) in a lactone form, comprising:

providing an amine salt of an HMG-CoA reductase inhibitor as a processing aid, starting substance, or an intermediate substance, wherein the said amine salt is formed from an amine selected from the group consisting of amines of the following formulae I and II:

a)

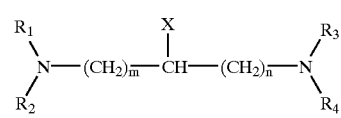

wherein:
a1) $R_1$, $R_2$, $R_3$ and $R_4$ independently denote:
a hydrogen atom;
a straight or a branched alkyl group having 1 to 8 carbon atoms;
a cycloalkyl group having 3 to 8 carbon atoms;
an arylalkyl group wherein the alkyl group is methyl or ethyl and the aryl group is phenyl, which is unsubstituted or substituted by an N-alkyl or N,N-dialkyl group wherein the alkyl group is alkyl having 1 to 4 carbon atoms;
an arylalkyl group which is unsubstituted or substituted by one or more substituents selected from the group consisting of a halogen, a hydroxyl group, an alkyl having 1 to 4 carbon atoms, an alkoxyl having 1 to 4 carbon atoms, an acyloxyl having 1 to 4 carbon atoms or an esterified carboxyl having 1 to 4 carbon atoms;
a hydroxyalkyl group having 2 to 4 carbon atoms; or
an aminoalkyl group having 2 to 4 carbon atoms, which are unsubstituted or substituted by an N-alkyl or N,N-dialkyl group wherein the alkyl group is alkyl having 1 to 4 carbon atoms;
X denotes a hydrogen atom, a hydroxyl group, a halogen or a methyl group;
m and n independently denote an integer from 0 to 5; or
a2) $NR_1R_2$ or $NR_3R_4$ denote a heterocyclic ring having 3 to 7 methylene groups, wherein these groups are unsubstituted or one of these groups is substituted by an oxygen or a sulfur atom or an imine group; and X, m and n are the same as defined above;

a)

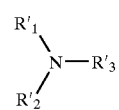

wherein:
b1) $R'_1$, $R'_2$, and $R'_3$ are the same or different and denote hydrogen, alkyl, alkenyl, amino- or hydroxy- or alkoxy- substituted alkyl or alkenyl, or substituted amino- alkyl or alkenyl wherein the amino group is substituted by one or more substituents selected from the group consisting of a halogen, a hydroxyl group, an alkyl having 1 to 4 carbon atoms, an alkoxyl having 1 to 4 carbon atoms, an acyloxyl having 1 to 4 carbon atoms and an esterified carboxyl having 1 to 4 carbon atoms, provided that R'$_1$, R'$_2$ and R'$_3$ are not hydrogen at the same time; or b2) R'$_1$, R$_2$, and R'$_3$, or R'$_1$ and R'$_2$, together with the nitrogen atom form a heterocyclic ring system with the nitrogen atom as the only hetero atom ring member, or a heterocyclic ring system with the nitrogen atom as a hetero atom and with an additional hetero atom ring member, and if R'$_3$ is not part of the ring system it is independently selected from hydrogen, alkyl, alkenyl, amino- or hydroxy- or alkoxy- substituted alkyl, or substituted amino- alkyl wherein the amino group is substituted by one or more substituents selected from the group consisting of a halogen, a hydroxyl group, an alkyl having 1 to 4 carbon atoms, an alkoxyl having 1 to 4 carbon atoms, an acyloxyl having 1 to 4 carbon atoms and an esterified carboxyl having 1 to 4 carbon atoms; or b3) R'$_1$ is a group of general formula III,

   III wherein m is zero or an integer from 1 to 5, R' is an aliphatic hydrocarbon cyclic system having 3 to 8 carbon atoms in the ring, wherein R' is unsubstituted or substituted by one or more substituents selected from the group consisting of a halogen, a hydroxyl group, an alkyl having 1 to 4 carbon atoms, an alkoxyl having 1 to 4 carbon atoms, an acyloxyl having 1 to 4 carbon atoms and an esterified carboxyl having 1 to 4 carbon atoms;

R'$_4$ is hydrogen, or alkyl, amino- or hydroxy- or alkoxy- substituted alkyl, or substituted amino- alkyl, wherein the amino group is substituted by one or more substituents selected from the group consisting of a halogen, a hydroxyl group, an alkyl having 1 to 4 carbon atoms, an alkoxyl having 1 to 4 carbon atoms, an acyloxyl having 1 to 4 carbon atoms or an esterified carboxyl having 1 to 4 carbon atoms;

or a group of the same general formula as R'$_1$ as defined herein above, R'$_2$ and R'$_3$ are the same as R'$_1$ or hydrogen, alkyl, alkenyl, amino- or hydroxy- or alkoxy- substituted alkyl, or substituted amino- alkyl or alkenyl, wherein the amino group is substituted by one or more substituents selected from the group consisting of a halogen, a hydroxyl group, an alkyl having 1 to 4 carbon atoms, an alkoxyl having 1 to 4 carbon atoms, an acyloxyl having 1 to 4 carbon atoms or an esterified carboxyl having 1 to 4 carbon atoms; or b4) R'$_1$ is an aryl group of general formula IV,

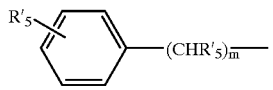   IV which is unsubstituted or substituted, wherein:

R'$_5$ is hydrogen or one or more substituents selected from the group consisting of a halogen, a hydroxyl group, an alkyl having 1 to 4 carbon atoms, an alkoxyl having 1 to 4 carbon atoms, an acyloxyl having 1 to 4 carbon atoms or an esterified carboxyl having 1 to 4 carbon atoms, and m is zero or an integer from 1 to 5, and R'$_2$ and R'$_3$ may be independently hydrogen, alkyl, amino- or hydroxy- or alkoxy- substituted alkyl, or substituted amino- alkyl, wherein the amino group is substituted by one or more substituents selected from the group consisting of a halogen, a hydroxyl group, an alkyl having 1 to 4 carbon atoms, an alkoxyl having 1 to 4 carbon atoms, an acyloxyl having 1 to 4 carbon atoms or an esterified carboxyl having 1 to 4 carbon atoms, or groups of the same general formula R'$_1$; and preparing the HMG-CoA reductase inhibitor using the amine salt of the HMG-CoA reductase inhibitor.

17. A process according to claim 16, wherein the amine is selected from the group consisting of (±)-1,2-dimethylpropylamine, 3-(2-aminoethylamino)-propylamine, n-butylamine, secondary butylamine, tertiary butylamine, dibutylamine, tertiary amylamine, cyclopentylamine, cyclohexylamine, cycloheptylamine, dicyclohexylamine, N-methylcyclohexylamine, N,N'-diisopropylethylenediamine, N,N'-diethylenediamine, N-methyl-1,3-propanediamine, N-methylethylenediamine, N,N,N',N'-tetramethyl-1,2-diaminoethane, N,N,N',N'-tetramethyl-1,4diaminobutane, N,N,N',N'-tetramethyl-1,6-diaminohexane, 1,2-dipiperidinethane, dipiperidinemethane, 2-amino-3,3-dimethylbutane, N,N-dimethylcyclohexylamine, neopentylamine, adamantylamine, N,N-diethylcyclohexylamine, N-isopropylcyclohexylamine, N-methylcyclohexylamine, cyclobutylamine and norborylamine.

18. The process according to claim 16, wherein the amine is selected from the group consisting of n-butylamine, secondary butylamine, tertiary butylamine, dibutylamine, tertiary amylamine, cyclohexylamine, dicyclohexylamine, N-methylcyclohexylamine and N,N'-diisopropylethylenediamine.

19. The process according to claim 16, wherein the HMG-CoA reductase inhibitor is selected from the group consisting of mevastatin, pravastatin, lovastatin, simvastatin, fluvastatin and atorvastatin.

20. The process according to claim 16, wherein said purified form is prepared by crystallization.

21. The process according to claim 16, wherein said modified form is prepared by chemical modification.

22. The process according to claim 16, wherein said modified form is prepared by biotechnological modification.

23. The process according to claim 16, wherein said pharmaceutically active salt form is the metal salt.

24. The process according to claim 16, wherein said pharmaceutically active salt is sodium salt or calcium salt.

25. A process for the isolation and/or purification of a HMG-CoA reductase inhibitor, characterized in that the amine salt of the HMG-CoA reductase inhibitor as defined in claim 16 is used for preparing and isolating the HMG-CoA reductase inhibitor by means of crystallization.

26. The process according to claim 25, wherein the amine salt of mevastatin, pravastatin, lovastatin, simvastatin, fluvastatin or atorvastatin is prepared and isolated.

27. A process according to claim 25, wherein the said amine salt of a HMG-CoA reductase inhibitor is a TBA salt of mevastatin, pravastatin, lovastatin, simvastatin, fluvastatin or atorvastatin.

28. A process for the isolation and/or purification of a HMG-CoA reductase inhibitor, characterized in that the amine salt of the HMG-CoA reductase inhibitor as defined in claim 16 is used for preparing and isolating the HMG-CoA reductase inhibitor by means of crystallization, wherein the prepared and isolated HMG CoA reductase is selected from the group consisting of mevastatin, pravastatin, lovastatin, simvastatin, fluvastatin or atorvastatin and has a HPLC purity of about 98%.

29. A process for the isolation and/or purification of a HMG-CoA reductase inhibitor, characterized in that the amine salt of the HMG-CoA reductase inhibitor as defined in claim 16 is used for preparing and isolating the HMG-CoA reductase inhibitor by means of crystallization, wherein the prepared and isolated HMG-CoA reductase is selected from the group consisting of mevastatin, pravastatin, lovastatin, simvastatin, fluvastatin or atorvastatin and has a HPLC purity above 99%.

30. A process for the preparation of a semisynthetic HMG-CoA reductase inhibitor comprising:
providing an amine salt of a HMG-CoA reductase inhibitor as defined-in claim 16; and
preparing the semisynthetic HMG-CoA reductase inhibitor using the amine salt of the HMG-CoA reductase inhibitor as a starting substance.

31. A process according to claim 30, wherein the amine is selected from the group consisting of (±)-1,2-dimethylpropylamine, 3-(2-aminoethylamino)-propylamine, n-butylamine, secondary butylamine, tertiary butylamine, dibutylamine, tertiary amylamine, cyclopentylamine, cyclohexylamine, cycloheptylamine, dicyclohexylamine, N-methylcyclohexylamine, N,N'-diisopropylethylenediamine, N,N'-diethylenediamine, N-methyl-1,3-propanediamine, N-methylethylenediamine, N,N,N', N'-tetramethyl-1,2-diaminoethane, N,N,N',N'-tetramethyl-1,4-diaminobutane, N,N,N', N'-tetramethyl-1,6-diaminohexane, 1,2-dipiperidinethane, dipiperidinemethane, 2-amino-3,3-dimethylbutane, N,N-dimethylcyclohexylamine, neopentylamine, adamantylamine, N,N-diethylcyclohexylamine, N-isopropylcyclohexylamine, N-methylcyclohexylamine, cyclobutylamine and norborylamine.

32. The process according to claim 30, wherein the amine salt of lovastatin is used as the starting substance for the preparation of simvastatin.

33. The process according to claim 30, wherein the TBA salt of lovastatin is used as the starting substance.

34. A process for the biotechnological modification of a HMG-CoA reductase inhibitor by using microorganisms or enzymatic systems thereof, characterized in that one of the components used in the medium is the amine salt of a HMG-reductase inhibitor as defined in claim 16.

35. The process according to claim 34, wherein the amine salt of mevastatin is used in the medium.

36. The process according to claim 34, wherein the amine salt of mevastatin is used in the medium and the amine is selected from the group consisting of (±)-1,2-dimethylpropylamine, 3-(2-aminoethylamino)-propylamine, n-butylamine, secondary butylamine, tertiary butylamine, dibutylamine, tertiary amylamine, cyclopentylamine, cyclohexylamine, cycloheptylamine, dicyclohexylamine, N-methylcyclohexylamine, N,N'-diisopropylethylenediamine, N,N'-diethylenediamine, N-methyl-1,3-propanediamine, N-methylethylenediamine, N,N,N', N'-tetramethyl-1,2-diaminoethane, N,N,N',N'-tetramethyl-1,4-diaminobutane, N,N,N, N'-tetramethyl-1,6-diaminohexane, 1,2-dipiperidinethane, dipiperidinemethane, 2-amino-3,3-dimethylbutane, N,N-dimethylcyclohexylamine, neopentylamine, adamantylamine, N,N-diethylcyclohexylamine, N-isopropylcyclohexylamine, N-methylcyclohexylamine, cyclobutylamine and norborylamine.

37. The process according to claim 34, wherein the amine salt of pravastatin is produced by the biotechnological process.

38. The process according to claim 35, wherein the amine salt of pravastatin is produced by the biotechnological process.

39. The process according to claim 36, wherein the amine salt of pravastatin is produced by the biotechnological process.

40. The process according to claim 35, wherein the amine salt of pravastatin is the TBA salt.

41. A process for the preparation of the a pharmaceutically acceptable salt of a HMG-CoA reductase inhibitor comprising:
providing an amine salt of the HMG CoA reductase inhibitor as defined in claim 16; and
preparing the pharmaceutically acceptable salt of the HMG-CoA reductase inhibitor using the amine salt of the HMG-CoA reductase inhibitor as a starting substance.

42. A process for the preparation of a pharmaceutically acceptable salt of a HMG-CoA reductase inhibitor comprising:
providing an amine salt of the HMG CoA reductase inhibitor as defined in claim 17; and
preparing the pharmaceutically acceptable salt of the HMG-CoA reductase inhibitor using the amine salt of the HMG-CoA reductase inhibitor as a starting substance.

43. A process for the preparation of a pharmaceutically acceptable salt of a HMG-CoA reductase inhibitor comprising:
providing an amine salt of the HMG CoA reductase inhibitor; and
preparing the pharmaceutically acceptable salt of the HMG-CoA reductase inhibitor using the amine salt of the HMG-CoA reductase inhibitor as a starting substance;
wherein the HMG CoA reductase inhibitor is selected from the group consisting of mevastatin, pravastatin, lovastatin, simvastatin, fluvastatin and atorvastatin.

44. The process according to claim 41, wherein the pharmaceutically active salt prepared is the metal salt.

45. The process according to claim 41, wherein the HMG-CoA reductase inhibitor prepared is the sodium salt of pravastatin or fluvastatin.

46. The process according to claim 41, wherein the HMG-CoA reductase inhibitor prepared is the calcium salt of atorvastatin.

47. A process for the preparation of a HMG-CoA reductase inhibitor in a lactone form comprising;
providing an amine salt of the HMG-CoA reductase inhibitor as defined in claim 16; and
preparing the HMG-CoA reductase inhibitor in the lactone form using the amine salt of the HMG-CoA reductase inhibitor as a starting substance.

48. The process according to claim 47, wherein the HMG-CoA reductase inhibitor prepared in the lactone form is lovastatin, mevastatin or simvastatin.

* * * * *